United States Patent [19]

Hara et al.

[11] Patent Number: 4,802,470
[45] Date of Patent: Feb. 7, 1989

[54] ELECTRIC FIELD THERAPY APPARATUS

[75] Inventors: Akikuni Hara; Yukio Ogawa, both of Tokyo, Japan

[73] Assignee: Hakuju Institute For Health Science Co., Ltd., Tokyo, Japan

[21] Appl. No.: 22,529

[22] Filed: Mar. 2, 1987

Related U.S. Application Data

[63] Continuation of Ser. No. 655,092, Sep. 27, 1984, abandoned.

[51] Int. Cl.⁴ .............................................. A61N 1/00
[52] U.S. Cl. .................................. 128/24.1; 128/783; 128/802
[58] Field of Search ........................ 128/24.1, 802, 783

[56] References Cited

U.S. PATENT DOCUMENTS

| | | | |
|---|---|---|---|
| 2,223,447 | 12/1940 | Hathaway | 128/802 |
| 4,175,551 | 11/1979 | D'Haenens et al. | 128/24.4 |
| 4,292,980 | 10/1981 | Suzuki | 128/783 |
| 4,419,995 | 12/1983 | Hochmair et al. | 128/784 |
| 4,472,661 | 9/1984 | Culver | 315/276 |

Primary Examiner—Leo P. Picard
Attorney, Agent, or Firm—Larson and Taylor

[57] ABSTRACT

An electric field therapy apparatus having electrodes connected to a pair of output terminals characterized in that an intermediate point between the output terminals is connected, as a voltage point, ground. With this arrangement, each of the electrodes can be constructed so as to make withstand voltage to ground small, and the electric potential difference between the electrodes can be made large.

4 Claims, 4 Drawing Sheets

ELECTRIC FIELD THERAPY APPARATUS

This application is a continuation of application Ser. No. 655,092, filed Sept. 27, 1984, now abandoned.

BACKGROUND OF THE INVENTION

The electric field therapy apparatus which serves to treat the human body in electric field and which is called electric potential, electrostatic, or ion therapy apparatus has been widely used as one means to attain physio-therapy and excellent therapeutical effects have been demonstrated. The feature of this electric field therapy apparatus exists in that therapeutical treatment can be easily effected all over the human body without current being applied directly to the human body.

FIG. 1 is a circuit diagram showing an example of the conventional electric field therapy apparatus. In FIG. 1, numeral 1 represents a boosting transformer, which is provided with a primary winding 2 and a secondary winding 3 which generates boosted voltage. Numerals 4, 4 denote power source terminals of a commerical power source E, 5,6 connecting points of the secondary winding 3, 7, 8 high impedance elements connected to the connecting points 5 and 6, respectively, and comprising resistors or capacitors, numerals 9, 10 connecting points, and numerals 11, 12 therapeutical electrodes, one 12 of which is connected to the earth 13 through the high impedance elements 8.

14 denote an earth connected to one line of the commercial power souce E. $V_1$ represents a voltage applied between the power source terminals 4 and 4 of the primary winding 2, and $V_2$ a voltage output between the connecting points 9 and 10.

In the case of the conventional electric field therapy apparatus arranged as described above, the side of the connecting point 6 of the secondary winding 3 is earthed, thereby enabling the electrode 12 to be of low withstand voltage to ground (dielectric strength against the voltage to ground, hereinafter referred to as "withstand voltage to ground") structure, but the side of the connecting point 5 of the secondary winding 3 is by about the voltage $V_2$ higher than the side of the connecting point 6 and this voltage $V_2$ is usually high, amounting to several kilo-volts, thereby causing the electrode 11 to be of high witstand voltage to ground structure.

When safety is considered, only the high impedance element 7 is sufficient, and the conventional apparatus is usually provided with only this high impedance element 7. When therapeutical effects attained by the electric field therapy apparatus are considered, the high impedance elements 7 and 8 are not necessarily needed.

SUMMARY OF THE INVENTION

The present invention relates to an improvement of the electric field therapy apparatus which uses high voltage to treat the human body and which is also called electric potential, electrostatic or ion therapy apparatus.

According to the present invention, the electric field therapy apparatus in which electrodes are connected to a pair of output terminals, respectively, is characterized in that an appropriate intermediate point between the output terminals is connected, as a voltage point, to the earth, that each of the electrodes is constructed so as to make withstand voltage to ground small, and that electric potential difference between the electrodes can be made large.

A first object of the present invention is to construct each of the electrodes so as to make withstand voltage to ground small.

A second object of the present invention is to make electric potential difference between the the electrodes large.

A third object of the present invention is to simplify the construction of each of the electrodes to make the whole of the apparatus small-sized.

These and other objects of the present invention can be achieved by an electric field therapy apparatus which is arranged according to the present invention, and some more concrete examples of this electric field therapy apparatus will be described in more detail with reference to the accompanying drawings. It should be understood that various changes and modifications of these examples are included within the scope of appended claims.

DETAILED DESCRIPTION OF THE PREFERRED EMBODIMENT

The present invention relates to an electric field therapy apparatus wherein an appropriate intermediate voltage point of terminal voltage on the secondary winding side of a boosting transformer is connected to the earth to make withstand voltage to ground of each of electrodes small and electric potential difference between the electrodes large.

Figure 1:
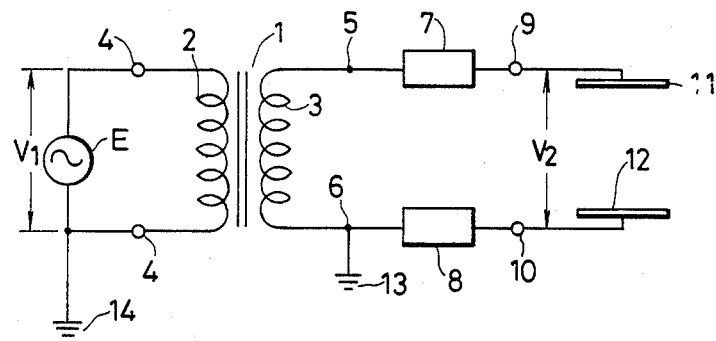
FIG. 1 is a circuit diagram showing an example of the conventional electric field therapy apparatus.
Figure 2A:
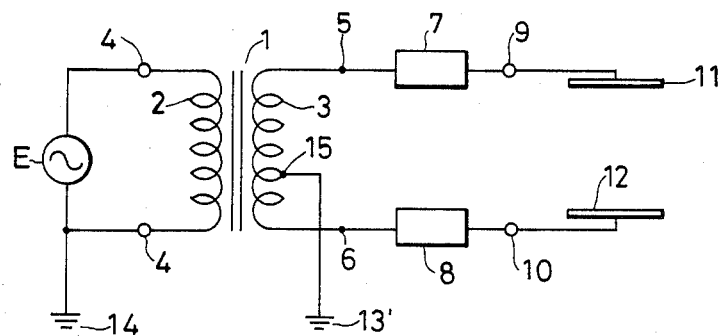
FIGS. 2a-2d are circuit diagrams showing an embodiment of the present invention.

FIG. 2a is a circuit diagram showing an embodiment of the present invention, in which same parts as those in FIG. 1 will be denoted by same reference numerals. Numeral 15 represents an intermediate tap positioned at a predetermined point of the secondary winding 3. This intermediate tap 15 is connected to the earth 13'.

The position of the intermediate tap 15 may not necessarily be the center of the secondary winding 3. Since the high impedance elements 7 and 8 are not necessarily needed from the viewpoint of therapeutical effects attained, they will be incorporated into the circuit, when needed.

Figure 2B:
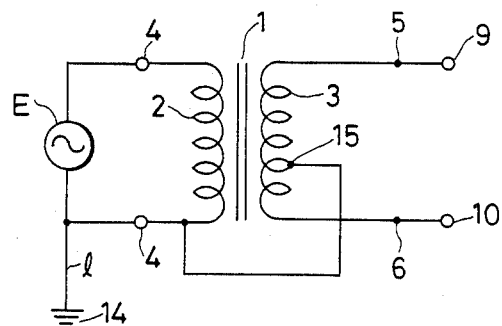

FIG. 2b shows an example wherein the intermediate tap 15 is connected to the primary winding 2 instead of its being directly earthed as shown in FIG. 2a, and wherein the intermediate tap 15 is earthed by connecting one line 1 of the commercial power source E to the earth 14.

Figure 2C:
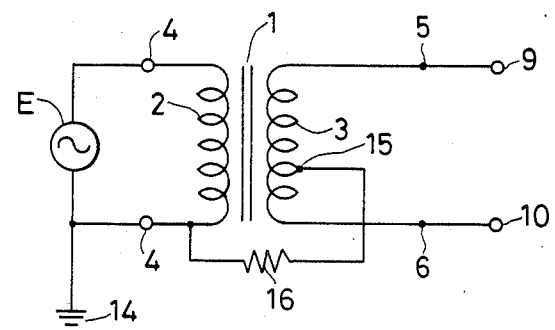

FIG. 2c shows another example wherein a safety resistor 16 is connected to the circuit shown in FIG. 2b.

Figure 2D:
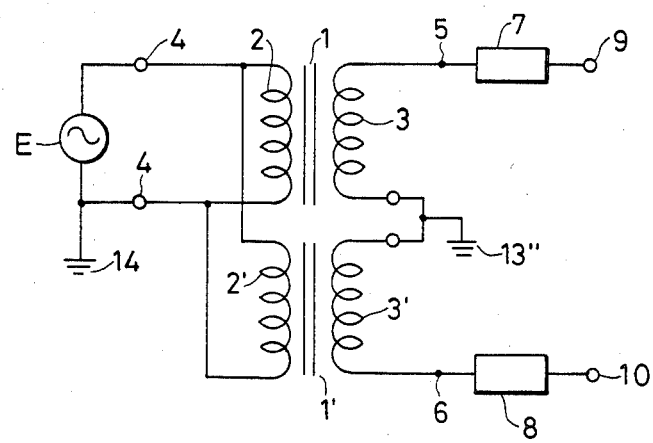

In FIG. 2d, two boosting transformers 1 and 1' are used and primary windings 2 and 2' are connected with each other in parallel while secondary windings 3 and 3' are connected with each other in series. The intermediate point between the secondary windings 3 and 3' connected is connected to the earth 13".

Figure 3:
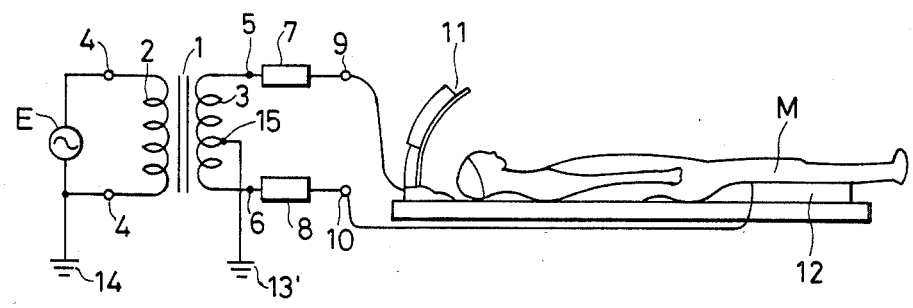
FIG. 3 is a view showing a case where the circuit shown in FIG. 2a is used.

FIG. 3 is a view showing a case where the circuit shown in FIG. 2a is used and M denotes a human body. The human body M to be treated is positioned between the electrodes 11 and 12. As apparent from the above, the electric field therapy apparatus of the present invention enables the withstand voltage to ground to be made small when voltage used is same as in the conventional case and the electric potential difference between the electrodes 11 and 12 to be made large when the withstand voltage to ground of the electrodes is same as in the conventional case.

FIGS. 4a–4e are circuit diagrams showing other embodiments of AC/DC superposed type according to the present invention where a part of the secondary winding side is shown, respectively. Same parts as those in FIG. 2a will be represented by same reference numerals.

Figure 4A:
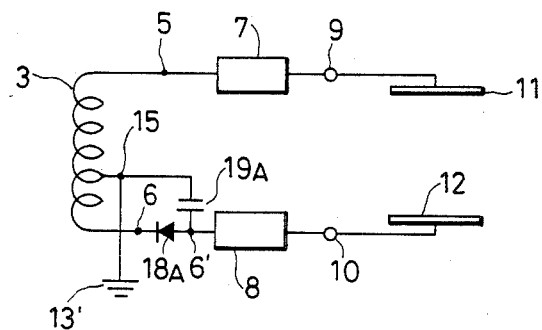
FIGS. 4a-4e are circuit diagrams showing other embodiments of the present invention.

In FIG. 4a, the intermediate tap 15 is connected to a connecting point 6' through a capacitor 19A and a diode 18A is interposed between the connecting point 6' and the connecting point 6 of the secondary winding 3. The example shown in FIG. 4a is same as that in FIG. 2a except the above. In this case, alternating current is applied between the earth and the electrode 11, while direct current is applied between the earth and the electrode 12.

Figure 4B:
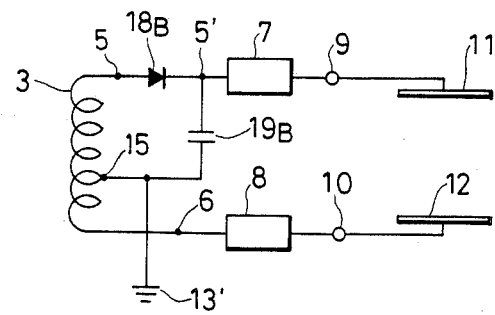

In FIG. 4b, the connecting point 5 of secondary winding 3 is connected to the high impedance element 7 through a diode 18B, and the intermediate tap 15 is connected to a connecting point 5' between the output side of the diode 18B and the high impedance element 7 through a capacitor 19B. The example in FIG. 4b is same as the one shown in FIG. 2a except the above. In this case, direct current is applied between the earth and the electrode 11, while alternating current between the earth and the electrode 12.

Figure 4C:
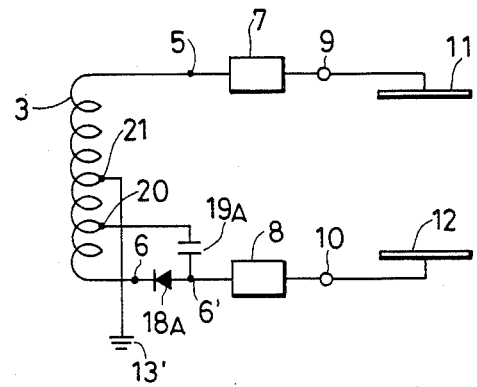

In FIG. 4c, two intermediate taps are arranged at the secondary winding 3 and represented by numerals 20 and 21 as first and second intermediate taps. The first intermediate tap 20 is connected to the connecting point 6' through the capacitor 19A, similarly to the case shown in FIG. 4a, and the diode 18A is interposed between the connecting point 6' and the connecting point 6 of the secondary winding 3. The second intermediate tap 21 is connected to the earth 13'. In this case, alternating and direct current is applied between the earth and the electrode 12, while alternating current between the earth and the electrode 11.

Figure 4D:
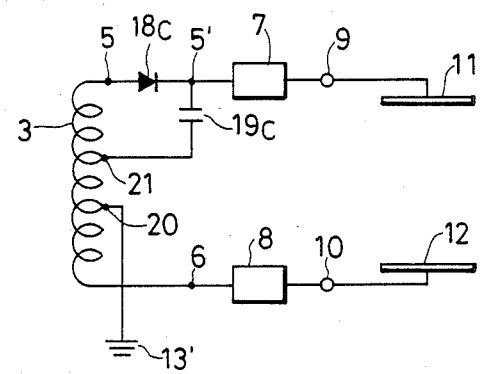

In FIG. 4d, the second intermediate tap 21 is connected to a connecting point 5' through a capacitor 19C and a diode 18C is interposed between the connecting point 5' and the connecting point 5 of the secondary winding 3. The first intermediate tap 20 is connected to the earth 13', similarly to the case shown in FIG. 2a. Alternating and direct current is applied between the earth and the electrode 11, while alternating current between the earth and the electrode 12.

Figure 4E:
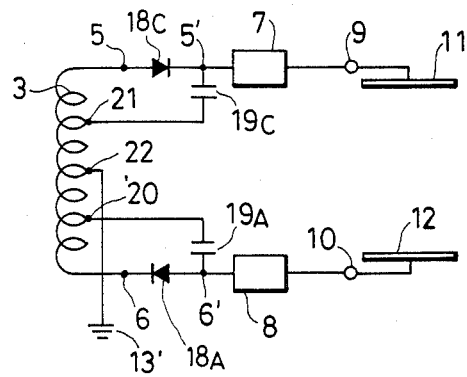

FIG. 4e shows a case where a third intermediate tap 22 is arranged at the secondary winding in addition to the first and second intermediate taps 20 and 21. The third intermediate tap 22 is connected to the earth 13'. This example in FIG. 4e corresponds to the combination of those shown in FIGS. 4c and 4d. Alternating and direct current is applied to the electrodes 11 and 12.

Even in the cases of these embodiments shown in FIGS. 4a–4e, the high impedance elements 7 and 8 are not necessarily needed, as described above.

In the cases of these embodiments shown in FIGS. 4a–4e, each of the intermediate taps 15, 20, 21 and 22 may be connected to the side of the primary winding 2, as shown in FIG. 2b, or a safety resistor may be interposed between each of the intermediate taps and the primary winding 2, as shown in FIG. 2c. The circuit shown in FIG. 2d may be employed.

As described above in detail, the intermediate tap is positioned at a certain point on the secondary winding of the boosting transformer in the case of the electric field therapy apparatus.

Therefore, the withstand voltage to ground of each of the electrodes may be adapted to be higher than voltage on the basis of the intermediate tap, thereby enabling the whole of the apparatus to be small-sized. Further, not earth electric potential (which is same in electric potential as the earth) but voltage corresponding to that at the intermediate tap is applied to the two electrodes, respectively. When a detector such as the neon tube is brought near one of the electrodes, therefore, it is turned on, thereby making it visible to the user that electric field is formed, so that relief and reliability can be quaranteed to the user, which is an extremely practical effect attained by the therapy apparatus.

What is claimed is:

1. An electric field therapy apparatus for treatment of the human body and the like, said apparatus comprising:
    a pair of spaced apart electrodes having a spacing therebetween that is large enough to receive a body part to be treated;
    terminal means for connecting said apparatus to a commercial power source of alternating current of a predetermined frequency;
    a transformer, having a primary winding connected across said terminal means and a secondary winding connected at two spaced apart points on said secondary winding to respective electrodes of said pair of electrodes, for boosting the voltage of said power source to provide a very high voltage of said predetermined frequency across said electrodes; and
    means for connecting a third point on said secondary winding, located between said two spaced part points, to ground.

2. An apparatus as claimed in claim 1 wherein said transformer comprises a boosting transformer and said third point comprises an intermediate tap between said spaced apart points on said secondary winding.

3. An apparatus as claimed in claim 1 wherein said apparatus comprises two of said transformers, said two transformers comprising first and second boosting transformers wherein the primary windings of said boosting transformers are connected in parallel and the secondary windings of said booster transformers are connected in series, said third point comprising a connecting point between the series connected secondary windings which is connected to ground.

4. An apparatus as claimed in claim 1 wherein said transformer comprises a boosting transformer and said third point comprises an intermediate tap which is positioned on said secondary windings between said spaced apart points on said secondary winding and which is connected to ground through a connection to the primary winding of said boosting transformer.

* * * * *